US010933084B2

(12) United States Patent
Cantor et al.

(10) Patent No.: US 10,933,084 B2
(45) Date of Patent: Mar. 2, 2021

(54) COMPOSITIONS AND METHODS FOR TREATING ELASTIC FIBER BREAKDOWN

(71) Applicant: MatRx Therapeutics Corporation, New York, NY (US)

(72) Inventors: Jerome O. Cantor, Brooklyn, NY (US); Gerard M. Turino, New York, NY (US)

(73) Assignee: MatRx Therapeutics Corporation, New York, NY (US)

( * ) Notice: Subject to any disclaimer, the term of this patent is extended or adjusted under 35 U.S.C. 154(b) by 0 days.

(21) Appl. No.: 16/383,033

(22) Filed: Apr. 12, 2019

(65) Prior Publication Data

US 2019/0314403 A1 Oct. 17, 2019

Related U.S. Application Data

(60) Provisional application No. 62/656,654, filed on Apr. 12, 2018.

(51) Int. Cl.
| | | |
|---|---|---|
| *A61K 31/728* | (2006.01) | |
| *A61P 11/00* | (2006.01) | |
| *A61K 9/00* | (2006.01) | |

(52) U.S. Cl.
CPC .......... *A61K 31/728* (2013.01); *A61K 9/0075* (2013.01); *A61K 9/0078* (2013.01); *A61P 11/00* (2018.01)

(58) Field of Classification Search
CPC ... A61K 31/728; A61K 9/0075; A61K 9/0078
See application file for complete search history.

(56) References Cited

U.S. PATENT DOCUMENTS

2002/0086852 A1* 7/2002 Cantor ................. A61K 9/0078
514/54

FOREIGN PATENT DOCUMENTS

| WO | WO-01/93846 A2 | 12/2001 |
| WO | WO-02/102317 A2 | 12/2002 |

OTHER PUBLICATIONS

Blackwood et al., "Glycosaminoglycan synthesis in endotoxin induced lung injury," Proc Soc Exp Biol Med 174(3):343-349 (1983).
Cantor et al., "A pilot clinical trial to determine the safety and efficacy of aerosolized hyaluronan as a treatment for COPD," Int J Chron Obstruct Dis 12:2747-2752 (2017).
Cantor et al., "Aerosolized hyaluronan limits airspace enlargement in a mouse model of cigarette smoke induced pulmonary emphysema," Exper Lung Res 31(4):417-430 (2004).
Cantor et al., "Aerosolized hyaluronic acid decreases alveolar injury induced by human neutrophil elastase," Proceedings Soc Exper Biol & Med 217(4):471-475 (1998).
Cantor et al., "Can Exogenously Administered Hyaluronan Improve Respiratory Function in Patients With Pulmonary Emphysema?" Chest 125(1):288-292 (2004).
Cantor et al., "Further investigation of the use of intratracheally administered hyaluronic acid to ameliorate elastase-induced emphysema," Ex Lung Res 23(3):229-244 (1997).
Cantor et al., "Modulation of air-space enlargement in elastase-induced emphysema by intratracheal instillment of hyaluronidase and hyaluronic acid," Exper Lung Res 21(3):423-436 (1995).
Cantor et al., "Pulmonary air-space enlargement induced by intratracheal instillment of hyaluronidase and concomitant exposure to 60% oxygen," Exper Lung Res 19(2):177-192 (1993).
Cantor et al., "Synthesis of cross-linked elastin by mesothelial cell culture," Proc Soc Exp Biol Med 181(3):387-391 (1986).
Cantor et al., "The effect of hyaluronan on elastic fiber injury in vitro and elastase-induced airspace enlargement in vivo," Proc Soc for Exp Biol & Med 225(1):65-71 (2000).
Cantor et al., "Therapeutic effect of hyaluronan on smoke-induced elastin fiber injury: Does delayed treatment affect efficacy?" Lung 189(1):51-56 (2011).
Chapman et al., "Intravenous augmentation treatment and lung density in severe alpha-1 antitrypsin deficiency (RAPID): a randomized double-blinded, placebo-controlled trial," Lancet (2015).
Dabrowski et al., "Collagen, glycosaminoglycans and histamine in lungs of Guinea pigs exposed chronically to cigarette smoke," Bull Acad Pol Des Sci 23(2):125-128 (1975).
Frances et al., "Role of hyaluronan and hyaluronan-binding proteins in lung pathobiology," Amer J Physiol 301(2):L137-L147 (2011).
Hardingham et al., "Proteoglycans: many forms and many functions," FASEB J 6(3):861-70 (1992).
International Search Report and Written Opinion for International Application No. PCT/US2019/027257 dated Jul. 17, 2019.
Klagas et al., "Decreased hyaluronan in airway smooth muscle cells from patients with asthma and COPD," Eur Respir J 34(3):616-28 (2009).
Knudson et al., "Hyaluronan-binding proteins in development, tissue homeostasis and disease," FASEB J 7(13):1233-1241 (1993).
Konno et al., "A biochemical study on glycosaminoglycans (mucopolysaccharides) in emphysematous and in aged lungs," Am Rev Respir Dis 126(5):797-801 (1982).
LeBaron et al., "Hyaluronate binding properties of versican," J Biol Chem 267(14):10003-10010 (1992).
Ma et al., "Alpha-1 Antitrypsin Augmentation Therapy and Biomarkers of Elastin Degradation," J COPD 10(4):473-81 (2013).
Ma et al., "Measurements of Desmosine and Isodesmosine by Mass Spectrometry in COPD," Chest 131(5):1363-1371 (2007).
Ma et al., "The detection and quantitation of free desmosine and isodesmosine in human urine and their peptide-bound forms in sputum," PNAS 100(22):12941-12943 (2003).

(Continued)

*Primary Examiner* — Pancham Bakshi
(74) *Attorney, Agent, or Firm* — Foley Hoag LLP; Lucas Watkins; Mohanad Mossalam

(57) ABSTRACT

The present disclosure relates to pharmaceutical compositions capable of regulating elastic fiber. The disclosure further relates to methods of treating elastic fiber-related disorders, such as COPD, by inhalation of low-molecular weight hyaluronic acid.

13 Claims, 2 Drawing Sheets

(56) References Cited

OTHER PUBLICATIONS

Ma et al., "The Effect of Alpha-1 Proteinase Inhibitor on Biomarkers of Elastin degradation in Alpha-1 Antitrypsin Deficiency: An Analysis of the RAPID/RAPID Extension Trials," J COPD Foundation 4(1):34-44 (2017).
McDevitt et al., "Cigarette smoke degrades hyaluronic acid," Lung 167(1):237-245 (1998).
Murakami et al., "Effect of hyaluronidase on porcine pancreatic elastase-induced lung injury," J of Japanese Resp Society 36(7):577-84 (1998).
Nakamura et al., "High, But Not Low, Molecular Weight Hyaluronan Prevents T-Cell-Mediated Liver Injury by Reducing Proinflammatory Cytokines in Mice," J Gastroent 39(4):346-354 (2004).
Petrigni et al., "Hyaluronic acid protects asthmatics from exercise-induced bronchoconstriction," J European Respiratory Society 16(Suppl31):4585 (2000).
Petrigni et al., "Hyaluronic acid, a novel way of protecting asthmatics from non-specific bronchoprovocation," J European Respiratory Society 16(Suppl31):4585 (2000).
Senior et al., "Chronic obstructive pulmonary disease (COPD)," Am J Resp Crit Care Med 157(4Pt2):S139-S147 (1998).
Toole, "Hyaluronan and its binding proteins, the hyaladherins," Curr Opin Cell Biol 2(5):839-44 (1990).
Turino, "Safety Study of CTZ-100 Inhalation Solution (Formerly ETX-100)" Clinical Trials.gov Identifier: NCT00993707 (2009).
Turino, "The pulmonary parenchyma: a dynamic matrix," Amer Rev Respir Dis 132(6):1324-1334 (1985).

* cited by examiner

| Time point | Hyaluronic acid (N) | Placebo (N) |
|---|---|---|
| Pretreatment | 19.6±2.1 (7) | 12.0±6.3 (2) |
| Week 1 | 12.0±1.1 (6) | — |
| Week 2 | 9.4±1.1 (5) | — |
| Week 3 | 5.8±0.6 (2) | — |

COMPOSITIONS AND METHODS FOR TREATING ELASTIC FIBER BREAKDOWN

RELATED APPLICATIONS

This application claims the benefit of priority to U.S. Provisional Patent Application No. 62/656,654, filed Apr. 12, 2018, the content of which is hereby incorporated herein by reference in its entirety.

BACKGROUND

The protease-antiprotease concept of lung interstitial injury has encouraged the use of elastase inhibitors as potential treatments for chronic obstructive pulmonary disease (COPD). However, aside from α-1 antiprotease (AAP) replacement therapy for AAP-deficient patients, this approach has met with little success, and clinical testing of various inhibitors has failed to produce a successful drug for COPD.

SUMMARY OF THE INVENTION

The present disclosure is based, at least in part, on the discovery that inhalation of hyaluronan (HA), a long-chain polysaccharide preferentially binds to lung elastic fibers, prevents elastolysis, and limits airspace enlargement in experimental models of pulmonary emphysema. Accordingly, in certain embodiments, the disclosure provides methods of treating elastic fiber related disorder by administering doses of low-molecular weight hyaluronic acid inhalation solution.

In one aspect, a pharmaceutical composition comprising hyaluronic acid, or a pharmaceutically acceptable salt thereof, wherein the hyaluronic acid has a weight average molecular weight ($M_w$) of about 50 to about 1000 kDa; and a pharmaceutically acceptable excipient, is provided. In another aspect, an inhaler comprising the pharmaceutical composition described herein, is provided. In still another aspect, a method for treating an elastic fiber-related disorder in a subject, comprising administering to the subject hyaluronic acid, or a pharmaceutically acceptable salt thereof, wherein the hyaluronic acid has a weight average molecular weight ($M_w$) of about 50 to about 1000 kDa, is provided.

DETAILED DESCRIPTION OF THE INVENTION

Figure 1:
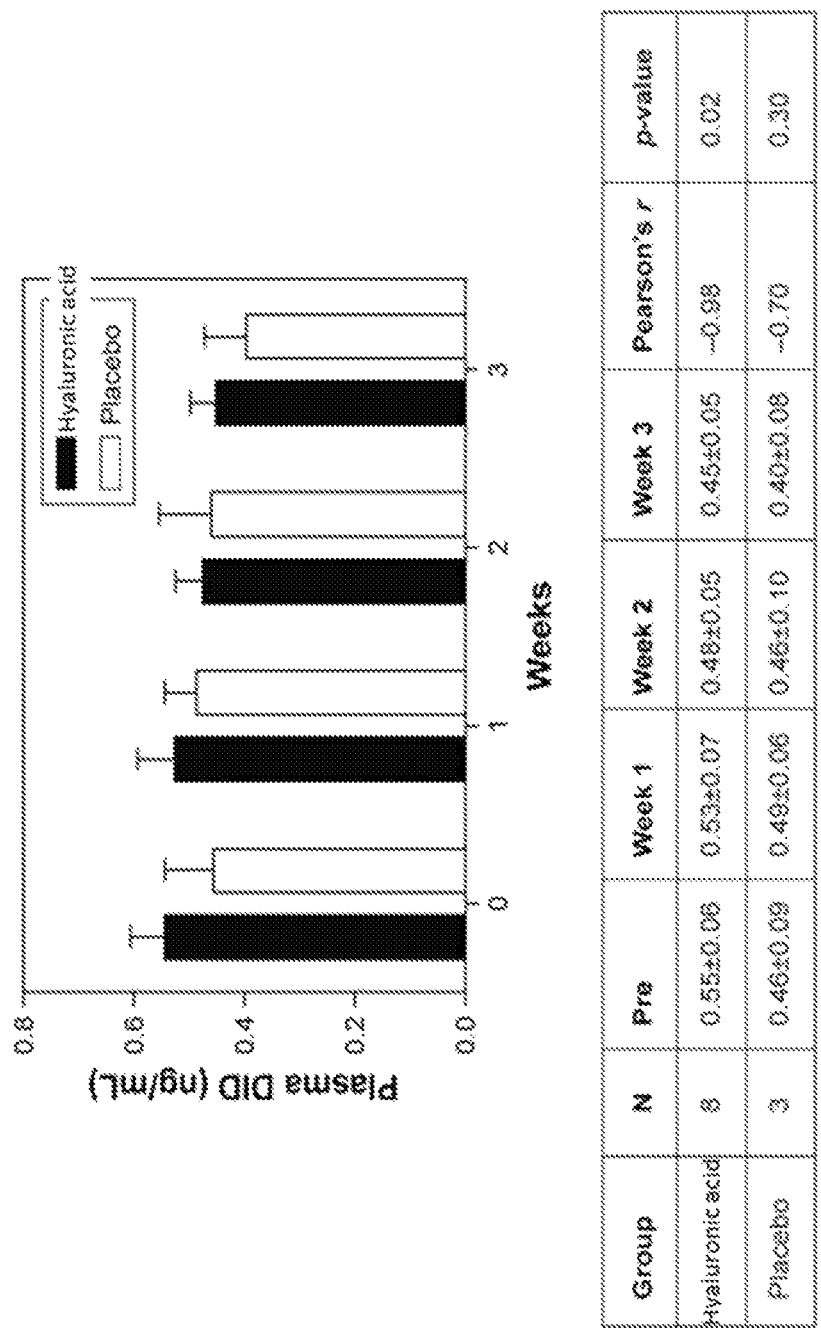
FIG. 1 shows a progressive reduction in plasma DID levels following treatment with HA (r=−0.98; p=0.02). Data are expressed as mean±SEM. Abbreviations: DID, desmosine and isodesmosine; SEM, standard error of the mean.

The present disclosure is based, at least in part, on the discovery that upon inhalation, hyaluronan (HA), a long-chain polysaccharide, preferentially binds to lung elastic fibers, prevents elastolysis, and limits airspace enlargement in experimental models of pulmonary emphysema. Desmosine and isodesmosine (DID) concentrations in plasma, sputum, and urine are measured as markers of elastin degradation systemically in the lung and also markers of inflammation and fibrinogen.

The results of the study in Example 1 indicate that aerosol administration of a 0.01% solution of low-molecular weight HA was well tolerated and did not involve adverse events requiring cessation of treatment. Moreover, there were significant reductions in the levels of DID in plasma and sputum, suggesting that nebulized HA is protecting elastin fibers from degradation and may therefore limit the development of pulmonary emphysema. In comparison to a recent trial involving long-term administration of AAP to chronic obstructive pulmonary disease (COPD) patients with AAP deficiency, the reduction in plasma levels of DID in the current study was greater and occurred more rapidly. The continued drop in both plasma and sputum DID levels during the week following cessation of treatment reflects the binding of HA to elastic fibers, which persists well beyond its half-life in the lung.

It is theorized that aerosolized fluorescein-labeled HA (150 kDa molecular weight) is able to enter the alveoli and preferentially binds to alveolar wall elastic fibers, presumably preventing interaction with injurious agents such as elastases and oxidants.

Aerosolized preparations of HA compounds have sometimes been used as therapeutic aerosols for certain upper respiratory disorders, but have not been tested for efficacy in other diseases or disorders, such as COPD. HA has also been used in patients with cystic fibrosis as an additive to hypertonic saline therapy. The HA used in these therapies has been prepared in high molecular weight forms (300-1,000 kDa). It is theorized that lower-molecular weight forms of HA, such as 150 kDa HA, have a lower viscosity and can achieve lower aerosol particle diameters, thereby facilitating their access to elastic fibers in the distal lung, whose destruction is a central feature of pulmonary emphysema.

While there are a number of animal studies indicating pro-inflammatory events associated with low-molecular-weight HA, the findings are generally associated with pre-existing acute lung injury, and so cannot be considered as representative of the chronic, subacute inflammatory process associated with COPD. Moreover, the clinical trial described herein showed no evidence of HA-induced inflammation, and long-term treatment of smoke-exposed animals with aerosolized HA did not show increased numbers of leukocytes, in either bronchoalveolar lavage fluid or histological sections of the lung.

Since elastic fiber breakdown may be a final common pathway in COPD, HA might be effective against a variety of injurious agents involved in the pathogenesis of this disease. In contrast to other proposed treatments, such as specific elastase inhibitors, HA might provide broader protection of the lung with fewer potential side effects. Furthermore, the generally slow progression of alveolar wall damage in COPD suggests that even small decreases in elastic fiber injury could significantly reduce the risk of respiratory failure.

Accordingly, in certain embodiments, the disclosure provides methods of treating elastic fiber related disorders by administering doses of low-molecular weight hyaluronic acid, for example as an inhalation solution.

Elastic fibers (or yellow fibers) are bundles of proteins (elastin) found in extracellular matrix of connective tissue and produced by fibroblasts and smooth muscle cells in arteries. Elastic fibers include elastin, elaunin and oxytalan. Elastic tissue is classified as "connective tissue proper". The elastic fiber is formed from the elastic microfibril (consisting of numerous proteins such as microfibrillar-associated glycoproteins, fibrillin, fibulin, and the elastin receptor) and amorphous elastin. Elastic fibers are found in the skin, lungs, arteries, veins, connective tissue proper, elastic cartilage, periodontal ligament, fetal tissue and other structures.

Non-limiting examples of elastic fiber related disorder are cutis laxa, Williams syndrome, alpha-1 antitrypsin deficiency (elastin is excessively degraded by elastase), emphysema, chronic obstructive pulmonary disease (COPD), liver disease, Buschke-Ollendorff syndrome, Menkes disease, pseudoxanthoma elasticum, Marfan's syndrome Hurler disease, hypertension and congenital heart defects.

In some aspects, a pharmaceutical composition comprising hyaluronic acid, or a pharmaceutically acceptable salt thereof, wherein the hyaluronic acid has a weight average molecular weight ($M_w$) of about 50 to about 1000 kDa; and a pharmaceutically acceptable excipient, is provided.

Numerous embodiments are further provided that can be applied to any aspect of the present disclosure. For example, in some embodiments, the hyaluronic acid has a weight average molecular weight ($M_w$) of about 50 kDa, about 60 kDa, about 70 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 kDa, about 230 kDa, about 240 kDa, about 250 kDa, about 260 kDa, about 270 kDa, about 280 kDa, about 290 kDa, about 300 kDa, about 400 kDa, about 500 kDa, about 600 kDa, about 700 kDa, about 800 kDa, about 900 kDa, and/or about 1000 kDa. In some embodiments, the hyaluronic acid has a weight average molecular weight ($M_w$) of 50-900 kDa, 50-800 kDa, 50-700 kDa, 50-600 kDa, 50-500 kDa, 50-400 kDa, 50-300 kDa, 50-290 KDa, 50-280 KDa, 50-270 KDa, 50-260 KDa, 50-250 KDa, 50-240 KDa, 50-230 KDa, 50-220 KDa, 50-210 KDa, 50-200 KDa, 50-190 KDa, 50-180 KDa, 50-170 KDa, 50-160 KDa, 50-150 KDa, 50-140 KDa, 50-130 KDa, 50-120 KDa, 50-110 KDa, or 50-100 KDa. In some embodiments, the hyaluronic acid has a weight average molecular weight ($M_w$) of about 150 kDa.

In some embodiments, the pharmaceutical composition described herein is in a form suitable for inhalation. In some embodiments, the pharmaceutical composition described herein is in a form suitable for nasal, intrapulmomary, intratracheal, intrabronchial, or intra-alveolar administration. In some embodiments, the pharmaceutical composition described herein is in a form suitable for intra-alveolar administration. In some embodiments, the pharmaceutical composition described herein is in a form suitable for administration through a dry powder inhaler. In some embodiments, the pharmaceutical composition described herein is in a form suitable for administration through a liquid spray device. In some embodiments, the liquid spray device is an aerosol device. In some embodiments, the aerosol device is a nebulizer or electrohydrodynamic aerosol device.

In some aspects, an inhaler comprising the pharmaceutical composition described herein, is provided.

Numerous embodiments are further provided that can be applied to any aspect of the present disclosure. For example, in some embodiments, the inhaler described herein is configured to deliver droplets with a size of 0.1-5 µm, 0.1-4 µm, 0.1-3 µm, 0.1-2 µm, 0.1-1 µm, 1-5 µm, 1-4 µm, 1-3 µm, 1-2 µm, 2-5 µm, 2-4 µm, 2-3 µm, 3-5 µm, 3-4 µm, or 4-5 µm. In some embodiments, the inhaler described herein is configured to deliver droplets with a size of about 0.1 µm, about 0.2 µm, about 0.3 µm, about 0.4 µm, about 0.5 µm, about 0.6 µm, about 0.7 µm, about 0.8 µm, about 0.9 µm, about 1 µm, about 1.5 µm, about 2 µm, about 2.5 µm, about 3 µm, about 3.5 µm, about 41 µm, about 4.5 µm, or about 5 µm. In some embodiments, the inhaler described herein is configured to deliver droplets with a size of 2 µm to 3 µm.

In some aspects, a method is provided for treating an elastic fiber-related disorder in a subject, comprising administering to the subject hyaluronic acid, or a pharmaceutically acceptable salt thereof, wherein the hyaluronic acid has a weight average molecular weight ($M_w$) of 50 to 1000 kDa.

Numerous embodiments are further provided that can be applied to any aspect of the present disclosure. For example, in some embodiments, the hyaluronic acid has a weight average molecular weight ($M_w$) of about 50 kDa, about 60 kDa, about 70 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 kDa, about 230 kDa, about 240 kDa, about 250 kDa, about 260 kDa, about 270 kDa, about 280 kDa, about 290 kDa, about 300 kDa, about 400 kDa, about 500 kDa, about 600 kDa, about 700 kDa, about 800 kDa, about 900 kDa, and/or about 1000 kDa. In some embodiments, the hyaluronic acid has a weight average molecular weight ($M_w$) of 50-900 kDa, 50-800 kDa, 50-700 kDa, 50-600 kDa, 50-500 kDa, 50-400 kDa, 50-300 kDa, 50-290 KDa, 50-280 KDa, 50-270 KDa, 50-260 KDa, 50-250 KDa, 50-240 KDa, 50-230 KDa, 50-220 KDa, 50-210 KDa, 50-200 KDa, 50-190 KDa, 50-180 KDa, 50-170 KDa, 50-160 KDa, 50-150 KDa, 50-140 KDa, 50-130 KDa, 50-120 KDa, 50-110 KDa, or 50-100 KDa. In some embodiments, the hyaluronic acid has a weight average molecular weight ($M_w$) of about 150 kDa. In some embodiments, the method described herein comprising administering the hyaluronic acid via inhalation. In some embodiments, the method described herein comprising administering the hyaluronic acid to the paranasal sinuses, the pulmonary system, the trachea, the bronchia, or the alveoli. In some embodiments, the elastic fiber-related disorder is cutis laxa, Williams syndrome, alpha-1 antitrypsin deficiency, emphysema, Chronic Obstructive Pulmonary Disease (COPD), liver disease, Buschke-Ollendorff syndrome, Menkes disease, pseudoxanthoma elasticum, Marfan's syndrome, Hurler disease, hypertension or a congenital heart defect. In some embodiments, the elastic fiber-related disorder is COPD.

Pharmaceutical Compositions

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the disclosure (e.g., hyaluronic acid of an appropriate molecular weight as disclosed herein) and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, aerosol, solution, syrup, suppository, injection or the like. The composition can also be present in a transdermal delivery system, e.g., a skin patch. The composition can also be present in a solution suitable for inhalation administration, such as a sprayed into the nose and absorbed through the nasal membranes (nasally) and/or Breathed into the lungs, through the mouth (by inhalation) or mouth and nose (by nebulization).

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 0.001 percent to about ninety-nine percent of active ingredient, preferably from about 0.01 percent to about 0.05 percent, most preferably from about 0.01 percent to about 0.03 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the disclosure with liquid carriers, or finely divided solid carriers, or both, and then, if necessary, shaping the product.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods provided in the present disclosure, active compounds can be given per se or as a pharmaceutical composition containing, for example, 0.01 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the disclosure may be used alone or conjointly administered with another type of therapeutic agent.

The present disclosure includes the use of pharmaceutically acceptable salts of compounds of the disclosure in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts. In certain embodiments, contemplated salts of the disclosure include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the present disclosure is directed to a packaged pharmaceutical composition comprising a container holding a therapeutically effective amount of a compound of the disclosure, alone or in combination with a second pharmaceutical agent; and instructions for using the compound to treat, prevent, or reduce one or more symptoms of a disease or disorder contemplated in the disclosure.

Formulations may be employed in admixtures with conventional excipients, i.e., pharmaceutically acceptable organic or inorganic carrier substances suitable for any suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., analgesic agents.

Routes of administration of any of the compositions of the disclosure include nasal, inhalational, intratracheal, intrapulmonary, intrabronchial, and inhalation.

Suitable compositions and dosage forms include, for example, dispersions, suspensions, solutions, syrups, granules, beads, powders, pellets, liquid sprays for nasal or oral administration, dry powder or aerosolized formulations for inhalation, and the like. It should be understood that the formulations and compositions that would be useful in the present disclosure are not limited to the particular formulations and compositions that are described herein.

Powdered and granular formulations of a pharmaceutical preparation of the disclosure may be prepared using known methods. Such formulations may be administered directly to a subject, used, for example, to form a material that is suitable to administration to a subject. Each of these formulations may further comprise one or more of dispersing or wetting agent, a suspending agent, and a preservative. Additional excipients, such as fillers and sweetening, flavoring, or coloring agents, may also be included in these formulations.

Pharmaceutical compositions of the present disclosure may be prepared, packaged, or sold in a formulation suitable for pulmonary administration via the buccal cavity. Such compositions may comprise dry particles that comprise the active ingredient and have a diameter in the range from about 0.5 to about 7 nanometers, and in certain embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain embodiments having a particle size of the same order as particles comprising the active ingredient).

Pharmaceutical compositions of the present disclosure formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration in certain embodiments have an average diameter in the range from about 0.1 to about 200 nanometers. In some embodiments, the droplets provided by this route of administration include a suitable amount of droplets (e.g., an amount of droplets sufficient to deliver a therapeutically effective dose to a target tissue as described elsewhere herein) with a diameter of 0.1-5 µm, 0.1-4 µm, 0.1-3 µm, 0.1-2 µm, 0.1-1 µm, 1-5 µm, 1-4 µm, 1-3 µm, 1-2 µm, 2-5 µm, 2-4 µm, 2-3 µm, 3-5 µm, 3-4 µm, or 4-5 µm. In certain embodiments, this route of administration provides a suitable amount of droplets with a diameter of about 0.1 µm, about 0.2 µm, about 0.3 µm, about 0.4 µm, about 0.5 µm, about 0.6 µm, about 0.7 µm, about 0.8 µm, about 0.9 µm, about 1 µm, about 1.5 µm, about 2 µm, about 2.5 µm, about 3 µm, about 3.5 µm, about 41 µm, about 4.5 µm, or about 5 µm. In certain embodiments, this route of administration provides a suitable amount of droplets with a diameter from about 2 μm to about 3 μm.

The pharmaceutical compositions of the present disclosure may be delivered using an inhalator such as those recited in U.S. Pat. No. 8,333,192 B2, which is incorporated herein by reference in its entirety.

The present disclosure provides methods for delivering medications deeper into the lungs and to the medications' pulmonary targets, which include bronchioles and alveoli. It is contemplated that a medication includes any particle, molecule or composition administered to a subject, human or animal, to achieve any desired result. For example, an aerosolized medication may be administered into a patient's respiratory tract, wherein the patient may be any animal or human subject. In some embodiments, an aerosolized surfactant is administered into the patient's respiratory tract that facilitates delivery of the aerosolized medication of the first step to the medication's pulmonary target. It is contemplated that, throughout this specification, the term "particle" or "particles" includes mixtures containing the medication or surfactant, droplets in which the medications or surfactants have been dissolved, solid medication or surfactant particles, and any other composition contemplated by one skilled in the art to contain the medication or surfactant being administered to the patient. The particles or droplets deposit on the luminal surface. The location for deposit of the particles depends on the inhaler characteristics and patient technique. The patient may then inhale a dose of the aerosolized surfactant from a second inhaler. The same effect can be obtained through the use of a tandem inhaler apparatus, or any other application that allows the smaller particles containing the medications to be delivered.

The compositions may also be administered directly to the lung by inhalation. Any suitable inhaler may be used, for example those disclosed in Tong et al., U.S. Pat. No. 6,251,941; Clark et al., U.S. Pat. No. 6,655,379, which are herein incorporated by reference. For administration by inhalation, the compositions may be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas may be used to deliver the composition directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device may be used to administer the composition to the lung (For suitable inhalers, see, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which may then be inhaled by the patient. DPI devices are also well known in the art and may be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of the compound and a suitable powder base such as lactose or starch for these systems.

Another type of device that may be used to deliver the composition to the lung is a liquid spray device supplied, for example, by Aradigm Corporation. Liquid spray systems use extremely small nozzle holes to aerosolize liquid drug formulations that may then be directly inhaled into the lung.

In some preferred embodiments, a nebulizer device is used to deliver the composition to the lung. Nebulizers create aerosols from liquid drug formulations by using, for example, ultrasonic energy to form fine particles that may be readily inhaled (See e.g., Verschoyle et al., British J. Cancer, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In some preferred embodiments, an electrohydrodynamic ("EHD") aerosol device is used to deliver the composition to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, U.S. Pat. No. 6,105,877; Coffee, U.S. Pat. No. 6,105,571; Coffee, PCT Application, WO 95/26234, Coffee, PCT Application, WO 95/26235, Coffee, PCT Application, WO 95/32807, which are herein incorporated by reference). The electrochemical properties of the composition formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other suitable methods of intrapulmonary delivery of the composition are within the scope of the disclosure.

Liquid drug formulations suitable for use with nebulizers and liquid spray devices and EHD aerosol devices will typically include the composition with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the composition. Preferably, this material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. No. 5,112,598; Biesalski, U.S. Pat. No. 5,556,611, which are herein incorporated by reference)

In certain embodiments, the composition of the disclosure comprises a stable dry powder blend containing levothyroxine sodium hydrate; lactose particles, comprising lactose $H_2O$, gelatin and starch maize; sodium starch glycolate; magnesium stearate; and talc silicified, comprising talc purified and colloidal silicon dioxide. In other embodiments, the dry powder comprises levothyroxine sodium is in an amount 4 to 0.02 mg per 100 mg of the dry powder. In yet other embodiments, the dry powder comprises lactose in an amount higher than 90 mg per 100 mg of the dry powder preparation. In yet other embodiments, the dry powder comprises lactose particles consisting of lactose $H_2O$, gelatin and starch maize, wherein the ratio by weight-mg of: "lactose $H_2O$":"gelatin":"starch maize" is 55-75:0.20-0.80:20-40. In yet other embodiments, the dry powder comprises sodium starch glycolate in an amount of 4-8 mg per 100 mg of dry powder. In yet other embodiments, the dry powder comprises magnesium stearate in an amount of 0.5-2 mg per 100 mg of dry powder. In yet other embodiments, the dry powder comprises talc silicified, in an amount of 2 mg per 100 mg of dry powder, wherein the talc silicified comprises talc purified and colloidal silicon dioxide in an amount of 0.667 mg of talc purified and 1.333 mg of colloidal silicon dioxide for 2 mg of talc silicified. In yet other embodiments, the blend further comprises a lake. In yet other embodiments, the dry powder comprises sodium starch glycolate in an amount of 5-6 mg per 100 mg of dry powder. In yet other embodiments, the dry powder comprises magnesium stearate in an amount of 1 mg per 100 mg of dry powder.

The formulations described herein as being useful for pulmonary delivery are also useful for intranasal delivery of a pharmaceutical composition of the disclosure.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

Definitions

For convenience, certain terms employed in the specification, examples, and appended claims are collected here.

As used herein, the singular forms "a", "an," and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising." The transitional terms "consist" and any grammatical variations thereof, are intended to be limited to the elements stated in the claims and exclude any elements not stated in the claims. The phrases "consisting essentially of" and any grammatical variant thereof indicate that the claim encompasses embodiments containing the specified elements and includes additional elements that do not materially affect the basic and novel characteristic(s) of the claim.

The term "about" or "approximately" means within an acceptable error range for the particular value as determined by one of ordinary skill in the art, which will depend in part on how the value is measured or determined, i.e., the limitations of the measurement system, and the conventional variability accepted in the art for the concerned parameter.

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Methods of Treatment

Provided herein are methods of treating elastic fiber related disorder. In certain embodiments, the present disclosure provides methods of treating elastic fiber related disorder by administering doses of low-molecular weight hyaluronic acid inhalation solution. Non-limiting examples of elastic fiber related disorder include cutis laxa, Williams syndrome, alpha-1 antitrypsin deficiency (elastin is excessively degraded by elastase), emphysema, liver disease, Buschke-Ollendorff syndrome, Menkes disease, pseudoxanthoma elasticum, Marfan's syndrome Hurler disease, hypertension and congenital heart defects.

EXAMPLES

The invention now being generally described, it will be more readily understood by reference to the following examples, which are included merely for purposes of illustration of certain aspects and embodiments of the present invention, and are not intended to limit the invention.

Example 1: Evaluate the Therapeutic Role of HA

To evaluate the therapeutic role of HA, a 2-week, randomized, double-blind, placebo-controlled, phase 2a safety trial was conducted in 11 patients with COPD. The primary aims of the study were: 1) to determine the safety of administering repeated doses of HA to subjects with smoking-related COPD and 2) to assess the effects of HA on elastin degradation, as measured by sputum and plasma levels of desmosine and isodesmosine (DID), cross-linking amino acids found only in this protein. The results indicate that inhalation of HA is well tolerated and rapidly reduces lung elastic fiber breakdown, thus supporting a longer-term investigation of the clinical efficacy of this agent.

Study Protocol

Eleven patients were recruited from 2 centers: 9 from Research Associates in Tucson, Ariz. and 2 from St Luke's-Roosevelt Hospital Pulmonary Disease Center in New York. The trial (NCT00993707) was conducted under IND number 70299, with Institutional Review Board approval from both organizations, and complied with the standards of Good Clinical Practice.

The patients ranged in age from 40 to 76 and fulfilled the diagnostic criteria of COPD with GOLD grades 2 and 3 with moderate airway obstruction (forced expiratory volume in 1 second above 40% of predicted) and at least a 10 pack-year history of cigarette smoking (Table 1). Ten were white and 1 was African-American. Informed consent was obtained from all participants.

TABLE 1

Patient characteristics.

| Characteristic | HA Treatment | Placebo |
|---|---|---|
| Number of subjects | 8 | 3 |
| Age (years) | 63 ± 8[a] | 52 ± 11[a] |
| Race | 7 white, 1 African-American | 3 white |
| FEV$_1$ (L) | 1.84 ± 0.45[a] | 1.77 ± 0.44[a] |
| DLCO (mL/min/mmHg) | 16.6 ± 8.0[a] | 19.6 ± 0.8[a] |
| Total lung capacity (L) | 7.1 ± 2.1[a] | 5.9 ± 0.5[a] |
| Smoking Hx | >10 pack-years | >10 pack-years |
| Active smokers | None | None |
| Inhaled corticosteroids | 4 | None |
| Recent exacerbations | None | None |

Note:
[a]Mean ± SD.
Abbreviations:
DLCO, carbon monoxide diffusing capacity;
FEV$_1$, forced expiratory volume in 1 second;
Hx, history;
SD, standard deviation.

None were actively smoking at the time of recruitment, and smoking cessation had occurred at least 1 year prior to the study. They were randomly assigned to treatment groups receiving either 0.01% HA BID (8 patients) or matching placebo (3 patients). All patients were instructed to continue their usual bronchodilator therapy during the trial.

Each patient self-administered 3 mL of aerosolized inhalation solution, using a Pari nebulizer, twice daily for 14 days. The primary safety end points were oxygen saturation, spirometry, lung volumes, physical examination, vital signs, electrocardiogram, and laboratory evaluations (complete blood count, serum chemistries, and urinalysis). Additionally, DID concentrations in sputum and plasma were measured prior to treatment with either HA or placebo, and again at weekly intervals, including the week following treatment.

HA Drug Preparation

The treatment agent used for the study consisted of 0.01% HA isolated from *Streptococcus equi* (150 kDa weight average molecular weight); dissolved in 3 mL of isotonic, buffered saline; and packaged in plastic vials under sterile conditions. The placebo consisted of identically packaged isotonic, buffered saline without HA.

Measurement of DID

Samples were combined with an equal volume of 37% HCl and hydrolyzed at 110° C. for 24 h, then dried under vacuum, suspended in 2 mL of butanol, acetic acid, and water (4:1:1), applied to a CF1 column, washed, and eluted. Separation of DID was performed with a 2×100 mm dC18 column (Waters Corporation, Milford, Mass., USA), using a combination of mobile phases: 1) 7 mM heptafluorobutyric acid and 5 mM ammonium acetate in water and 2) 7 mM heptafluorobutyric acid and 5 mM ammonium acetate in 80% acetonitrile. The elution gradient was programmed linearly from 100% A to 90% A over a 10-min interval, and the separated crosslinks were analyzed with a TSQ Discovery electrospray tandem mass spectrometer (Thermo Fisher Scientific, Waltham, Mass., USA), using selected reaction monitoring of mass-to-charge ratio transitions. The results were quantified by comparison with an external d4-labeled desmosine standard and the sputum results were normalized to total protein, as measured by a Micro BCATM assay kit (Thermo Fisher Scientific, Springfield Township, N.J., USA).

Statistical Analysis

Statistically significant correlations ($p<0.05$) between DID levels and length of time following treatment were determined by performing a two-tailed t-test on the Pearson coefficient (r). Results were expressed as mean±standard error of the mean for plasma and sputum DID levels and as mean±standard deviation for all other measurements.

Safety Assessment

The administration of HA had no significant effect on spirometry, lung volumes, electrocardiograms, and hematological indices. In particular, forced expiratory volume measurements at 1 second showed no significant changes during the course of the study, which included a 1-week interval posttreatment (Table 2). Similarly, carbon monoxide diffusing capacity remained unchanged during the 2-week trial (Table 3). Adverse events were generally mild and recurred with greater frequency in the placebo group (Table 4). None could be directly attributed to the inhalation procedure.

TABLE 2

FEV$_1$ (liters ± SD).

| Time point | HA[a] | Placebo[b] | p-value |
|---|---|---|---|
| Pretreatment | 1.84 ± 0.45 | 1.77 ± 0.44 | 0.92 |
| Week 1 | 1.80 ± 0.42 | 1.75 ± 0.38 | 0.92 |
| Week 2 | 1.72 ± 0.33 | 1.73 ± 0.31 | 1.0 |
| Week 3 | 1.90 ± 0.51 | 1.70 ± 0.29 | 0.36 |

Note:
[a]N = 8,
[b]N = 3.
Abbreviations:
FEV$_1$, forced expiratory volume in 1 second;
SD, standard deviation.

TABLE 3

DLCO (mL/min/mmHg ± SD).

| Time point | HA[a] | Placebo[b] | p-value |
|---|---|---|---|
| Pretreatment | 16.6 ± 8.0 | 19.6 ± 0.8 | 0.54 |
| Week 1 | 16.2 ± 7.8 | 19.8 ± 1.5 | 0.46 |
| Week 2 | 15.6 ± 6.9 | 19.8 ± 1.0 | 0.34 |

Note:
[a]N = 8,
[b]N = 3.
Abbreviations:
DLCO, carbon monoxide diffusing capacity;
SD, standard deviation.

TABLE 4

Adverse events.

| HA | Placebo |
|---|---|
| Migraine[a] | Difficulty breathing[a] |
| Joint pain[b] | Lung pain[a] |
| Chest congestion[b] | Profuse sweating[a] |
| Fever[b] | Coughing[b] |
| Intermittent cough[b] | Light-headedness[b] |
| Pitting edema[b] | |
| Diarrhea[b] | |
| Light-headedness[b] | |

Note:
[a]Moderate,
[b]mild.

Biomarker Measurements

Figure 2:
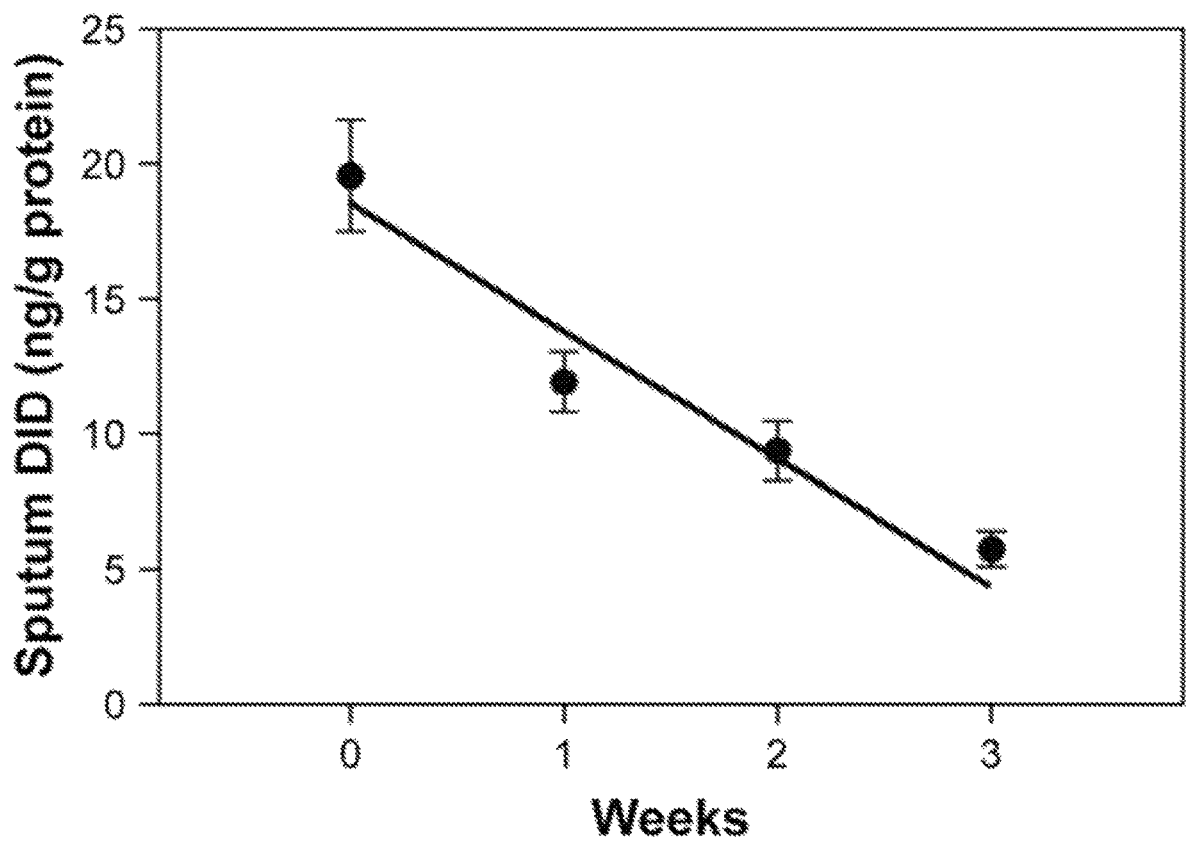
FIG. 2 shows a statistically significant negative correlation between sputum DID levels and time following treatment with HA (r=−0.97; p=0.03). Data are expressed as mean±SEM. Abbreviations: DID, desmosine and isodesmosine; SEM, standard error of the mean.

The HA group showed a progressive decrease in plasma DID levels over a 3-week period following initiation of treatment (r=−0.98; p=0.02; FIG. 1). In contrast, there was no significant reduction in the placebo group (r=−0.70; p=0.30). Sputum DID levels, which specifically reflect lung elastin degradation, also showed a progressive decrease over the same time interval (r=−0.97; p=0.03; FIG. 2).

Example 2: Evaluate the Therapeutic Role of HA

To further to evaluate the safety and efficacy of administering repeated doses of Hyaluronic Acid Inhalation Solution to subjects with Emphysema that have Alpha-1-Antitrypsin deficiency, a randomized, double-blind, placebo-controlled, phase 2 safety trial is conducted. The study primarily aims to establish desmosine and isodesmosine concentrations in plasma, sputum and urine measured as markers of elastin degradation systemically in the lung and also markers of inflammation and fibrinogen.

HA Drug Preparation: Hyaluronic Acid Inhalation Solution

The treatment agent (Hyaluronic acid) used for the study consists of 0.03% Hyaluronic Acid dissolved in 3 ml of Inhalation Solution and is administered twice a day. The placebo consists of the inhalation solution without HA.

Inclusion Criteria:

Men or women aged 18 through 80 years at the time of consent, Diagnosis of emphysema at screening consistent with National Institutes of Health guidelines 19 GOLD COPD classification stages I, II or III, Evidence of emphysema on radiographic imaging, A ratio of pre-bronchodilator FEV1 to forced vital capacity (FVC) of ≤80% at screening, FEV1≥30% and ≤79% (post-bronchodilator) of predicted normal at screening, Clinical laboratory tests (complete blood count, serum chemistry, and urinalysis) within normal limits or clinically acceptable to the PI and sponsor at screening, Evidence of alpha-1 antitrypsin deficiency (AATD) with any genotype except PiMZ deficiency, Patients must have stopped using Intravenous alpha-1 antitrypsin protein (AAT) augmentation therapy at least 3 months before entering study.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method for treating an elastic fiber injury in a human, comprising administering to the human 3 ml of a solution of 0.01% to 0.06% w/v of hyaluronic acid, or a pharmaceutically acceptable salt thereof, wherein the hyaluronic acid has a weight average molecular weight ($M_w$) of about 50 to about 1000 kDa.

2. The method of claim 1, wherein the hyaluronic acid has a weight average molecular weight ($M_w$) of about 150 kDa.

3. The method of claim 1, comprising administering the hyaluronic acid via inhalation.

4. The method of claim 1, comprising administering the hyaluronic acid to the paranasal sinuses, the pulmonary system, the trachea, the bronchia, or the alveoli.

5. The method of claim 1, wherein the hyaluronic acid is in a form suitable for inhalation.

6. The method of claim 5, wherein the hyaluronic acid is in a form suitable for nasal, intrapulmonary, intratracheal, intrabronchial, or intra-alveolar administration.

7. The method of claim 6, wherein the hyaluronic acid is in a form suitable for intra-alveolar administration.

8. The method of claim 1, wherein the hyaluronic acid is in a form suitable for administration through a liquid spray device.

9. The method of claim 8, wherein the liquid spray device is an aerosol device.

10. The method of claim 9, wherein the aerosol device is a nebulizer or electrohydrodynamic aerosol device.

11. The method of claim 1, wherein the aerosol is administered once or twice daily.

12. The method of claim 1, wherein the hyaluronan is administered from a vialed volume of 3 ml by aerosol from a nebulizer, once or twice daily.

13. The method of claim 1, wherein the patient has COPD or cystic fibrosis.

* * * * *